United States Patent [19]

Rosenblatt

[11] 4,098,728

[45] Jul. 4, 1978

[54] MEDICAL SURGICAL SPONGE AND METHOD OF MAKING SAME

[76] Inventor: Solomon Rosenblatt, 46 After Glow Ave., Montclair, N.J. 07042

[21] Appl. No.: 646,400

[22] Filed: Jan. 2, 1976

[51] Int. Cl.$^2$ .............................................. C08J 9/30
[52] U.S. Cl. .................................. 521/141; 260/42.51; 260/42.53; 260/42.54; 521/65; 521/905
[58] Field of Search ............... 260/2.5 F, 2.5 R, 2.5 L

[56] References Cited

U.S. PATENT DOCUMENTS

| | | | |
|---|---|---|---|
| 2,609,347 | 9/1952 | Wilson | 260/2.5 F |
| 2,653,917 | 9/1953 | Hammon | 260/2.5 F |
| 2,664,366 | 12/1953 | Wilson | 260/2.5 F |
| 2,664,367 | 12/1953 | Wilson | 260/2.5 F |
| 2,846,407 | 8/1958 | Wilson | 260/2.5 F |
| 3,663,470 | 5/1972 | Nishimura et al. | 260/2.5 F |
| 3,737,398 | 6/1973 | Yamaguchi | 260/2.5 F |

*Primary Examiner*—Morton Foelak

*Attorney, Agent, or Firm*—Ostrolenk, Faber, Gerb & Soffen

[57] ABSTRACT

A uniformly expandable hydrophilic sponge, adapted for medical usage, characterized by instantaneous wicking and a high liquid holding capacity comprising a reaction product of polyvinyl alcohol and formaldehyde. The wicking and liquid holding capacity is attained by controlling the time, temperature and processing conditions while forming and curing the reaction product in an aqueous medium. The sponge is rendered uniformly expandable by drying the wet sponge while maintaining the shape of the wet sponge. The sponge can be made X-ray opaque by incorporating, homogeneously, throughout an encapsulated radiopaque substance with the formaldehyde and polyvinyl alcohol. The sponge is biocompatible, non-toxic, lint free, compressible, resilient, strong, non-abrasive, free of foreign leachable materials and is of exceptionally high fluid holding capacity.

9 Claims, No Drawings

MEDICAL SURGICAL SPONGE AND METHOD OF MAKING SAME

BACKGROUND OF THE INVENTION

This invention relates to a hydrophilic sponge, adapted for medical and particularly surgical usage, comprising the reaction product of polyvinyl alcohol and formaldehyde. The sponge when wet with body fluids has a smooth and non-abrasive soft texture, is lint free, even when used abradably, is of exceptionally high fluid holding capacity, is compressible, flexible and resilient.

Medical sponges have many fluid absorbing applications including bandages for cuts and bruises, sanitary napkins for feminine hygiene, diagnostic swab "mailers" upon which bacteria can be cultured, general surgical sponges and specialty surgical sponges adapted for orthopedic, vascular, plastic, eye, ear, nose and throat use, among other known applications. As is described in U.S. Pat. No. 3,566,871, surgical sponges are used to remove body fluids such as blood, serum, plasma, lymph, spinal fluid, tissue fluid, urine, sweat, bile juice, and digestive juice. In the practice of surgery following an initial incision, it is customary to blot the incision and the adjacent area with sponges to remove blood and other fluids emanating from that incision. During internal surgery, for example, when operating in the thoracic cavity or abdominal cavity, sponges are used both to absorb blood and to isolate various organs from the operating field. The latter is accomplished by packing those organs with sponges to restrain them from interfering with the operation. The packing sponges are customarily pre-moistened in saline solution to prevent drying out organs or tissue with which they come into contact.

The sponge most commonly used today is a cellulose derived pad that may be of woven cotton, nonwoven cellulose or a felt made of rayon. However, cellulose pads tend to fragment and may shed lint thereby depositing biologically incompatible foreign substances in critical sites which can lead to the formation of brain or pulmonary emboli. As such, the fragments may also serve as a carrier for bacteria present in nonsterile areas of the operating room. The cellulose dust generated by opening a package of gauze pads may also lay down on the surface of open vessels of injectable solutions in the operating room enabling cellulose fragments to enter the blood stream directly. The gauze pad fragments left on internal organs also give rise to an adverse inflammatory reaction in the body, such as granulomater or adhesions.

Furthermore, gauze pads are known to be abrasive especially when dry. During use, as they absorb blood and body fluids, they tend to ball up and become increasingly harder and less pliable and therefore exhibit correspondingly increased abrasiveness. That is true notwithstanding the fact that the gauze pads were pre-moistened with saline solution. Since surgical pads may have to be moved or repositioned during an operation, abrasiveness of the pad can lead to trauma and inflammation.

Gauze pads used in surgery have the further disadvantage that they may not readily be shaped other than square or rectangular. That is due to their property of fraying and tendency to shed fragments. Thus, a surgeon cannot readily cut gauze pads to adapt them to a particular use.

Another problem with gauze pads is that they do not have a high capacity for holding fluid which increases the number of pads needed for a given medical procedure. In general their fluid holding capacity is limited to about 6 to 7 times the weight of the dry gauze. It would be greatly desirable to provide a pad capable of absorbing more than about 20 times its weight so as to reduce the need for replacing the pads during an operation.

The aforementioned U.S. Pat. No. 3,566,871 seeks to resolve the above problems associated with the use of gauze pads by means of a sponge made of polyurethane. That sponge is described as overcoming, for the most part, the problems of the gauze pad. The polyurethane sponge pad apparently does overcome some of the deficiencies of the gauze pad but in doing so it also appears to generate new problems of its own. For example, the polyurethane sponge described therein is impregnated with a hydrophilic surfactant absorbed into the sponge pores. The difficulty with that sponge, is that it contains a surfactant designed to render it artificially hydrophilic since polyurethane generally is otherwise hydrophobic. Those surfactant agents or substances have a tendency to leach out in the bloodstream. Although designed to absorb blood and body fluids upon contact, without compression, the fact remains that during the course of an operation, limitations of working space within the body make it highly unlikely that the surgeon will completely avoid making some contact with the sponges. Thus, when viewed pragmatically, particularly in the course of surgery, some compression of the sponges used is likely to occur. The significance of that compression, even if occasional, is that upon such compression the polyurethane sponge will release not only the blood and fluids absorbed, but also surfactant. That surfactant is a foreign substance and the body reacts to it just as it would to any foreign substance. Although described as substantially free of toxicity, it is in fact, and to varying degrees, toxic.

The polyurethane sponge also suffers from other deficiencies. Among its shortcomings is the fact that it remains somewhat abrasive. If particles should break off from the main sponge, the particles are not biocompatible. The sponge is not compressible for packaging and handling purposes. It does not completely resolve the problem of linting, is non-compressible, is friable, may yellow with age, and it is difficult to control the pore size of the sponge. Pore size control is of particular significance for precision work such as for neurosurgical or opthalmic surgical sponge instruments. For example, in opthalmic surgery it is most important that the sponge used to pick up blood and vitrous fluids which is commonly in the shape of a sponge-tipped spear and generally referred to as an "eye spear" has a definite smooth, predictable boundary. If an eye spear has large pores, its cut edge could have a half-moon shaped or swiss-cheese-like indentation. That would adversely affect the precision with which the eye surgery could be performed, e.g. the fine sutures used in eye surgery may get caught in the rough edges of the sponge. Thus a small uniform pore size distribution is desirable for eye surgical sponges. On the other hand, if a sponge is to be used for routine surgical procedures, e.g. soaking blood, a larger pore size would be acceptable.

One characteristic common to virtually all known surgical sponges used in internal surgery is that they are tagged with thin strips of radiopaque markers. Such radiopaque markers are visible by X-ray fluoroscopy. Thus, following surgery, a patient may be X-rayed to locate or help determine the presence of a sponge that may have slipped from view in the operative field. The difficulty with such radiopaque markers is that their visibility is limited by their size. X-ray opaque strips used on present gauze pads are made by mixing 6–12% barium sulfate with a resin such as polyethylene and extruding the resultant composition into a rod of about 1/16-inch diameter. The rod is heat sealed to the pad surface. The pad then is folded 12 to 15 times with the strip contained therein. As a practical matter, it would greatly facilitate determining the location of a sponge if the entire sponge was radiopaque and thus visible upon X-ray. However, this improved radiopacity must be achieved without altering fluid capacity or leaching of the radiopaque material from the sponge so that a foreign body toxic reaction is avoided.

Reaction products of polyvinyl alcohol and formaldehyde also have been used to produce sponge material, which material has been used as a washcloth, synthetic chamois skin, and the like. U.S. Pat. No. 2,609,347 describes sponges made by reacting polyvinyl alcohol and formaldehyde. The sponges made as described in said patent are intended for use as washcloths or chamois skin. Past efforts to use the sponge clinically for skin grafts and implantation in living tissue proved for the most part unsuccessful. This result is primarily due to possible toxic residues leaching from the sponge resulting in unreliable biocompatibility.

Furthermore, the sponges produced by the process described in U.S. Pat. No. 2,609,347 are undesirable for surgical sponges since they are not characterized by a pore geometry and size necessary for fast wicking, high liquid holding capacity and precision sponge instrument design. Fast wicking is highly desirable, since a sponge, in the dry state, is relatively abrasive and it is desirable to minimize abrasiveness quickly. The process described in this patent also is deficient for surgical purposes since no means are provided for assuring that the sponges produced will expand uniformly. This characteristic is essential since the utility of a medical sponge instrument is also dependent upon its predictable shape during use. This requires that a dry sponge, which is cut and compressed to a desired shape prior to use retains that shape and expands to a predictable volume during liquid absorption. Furthermore, the sponge described in this patent is undesirable since its liquid holding capacity is only in the order of 10 to 13 times the weight of the sponge.

Accordingly, it would be desirable to provide a soft non-toxic uniformly expandable medical sponge having a high fluid holding capacity and fast wicking which is lint free, even when cut or trimmed to a smaller size. Furthermore, it would be desirable to provide a medical sponge which is non-abrasive to delicate tissue and is capable of being rendered homogeneously radiopaque without incorporating a leachable X-ray opaque material into the sponge. In addition, it would be desirable to provide such a sponge which can be formed in a manner such that the size and geometry of the sponge pores can be regulated to conform to the desired pore size distribution required for fast wicking, high liquid holding capacity, and precision design. Also, it would be desirable to provide a sponge, which when expanded by virtue of liquid absorption, will expand to a predictable shaped volume.

SUMMARY OF THE INVENTION

The present invention is based upon discovery that by reacting polyvinyl alcohol and aqueous formaldehyde solution in the presence of an acid catalyst under carefully controlled conditions, a medical sponge having controlled pore size uniformly distributed throughout its volume can be obtained that is expandable, biocompatible, lint free, soft, has fast wicking, and has a high liquid holding capacity. Instantaneous wicking and high liquid holding capacity is attained by controlling the temperature and time conditions and processing procedure by which the formaldehyde and polyvinyl alcohol are mixed and reacted. The formaldehyde and polyvinyl alcohol are mixed warm in the presence of a surfactant to entrain air and to form pores having a more fibrous thin walled cell geometry and a uniform size distribution, to maintain the distribution of the pores so formed and to regulate excessive internal merging of the pores. After reaction and casting, the sponge is heated to quickly cure the outer surface thereof and thus form a relatively stable overall shape. Thereafter, the entire sponge is cured so that the entire sponge experiences minimum shrinkage during the curing cycle. The cured sponge is washed to remove the surfactant, acid and unreacted formaldehyde, the wet sponge is frozen, cut to shapes, defrosted, washed again and dried by heating the sponge between vapor permeable sponge sheets so that the entire sponge experiences uniform shrinkage during the drying step. This drying procedure assures subsequent uniform expansion of the sponge when it is compressed and then re-expanded during the absorption of liquid, thereby retaining its shape during liquid absorption and expansion.

DESCRIPTION OF SPECIFIC EMBODIMENTS

The sponge of this invention is formed by a plurality of steps wherein the process conditions such as reaction time, temperature, reactant ratios, mixing procedure, etc. are carefully controlled.

Polyvinyl alcohol and formaldehyde are reacted in an aqueous system having air bubbles uniformly dispersed therein in the presence of an inorganic acid catalyst. The reaction is carried out in the presence of a non-toxic surfactant which is added in order to aid in forming and stabilizing the gas bubbles formed uniformly throughout the reaction system. The reaction is carried out in two stages. In the first stage, the polyvinyl alcohol catalyst and wetting agent are combined and are subjected to agitation to entrap air bubbles uniformly throughout the reaction system and to form a froth having a volume between 150 and 400% of the volume of the reactants in an unfrothed condition. During the second stage, reaction between the polyvinyl alcohol and the formaldehyde is carried out while mixing is maintained during the polymerization to achieve a more fibrous thin walled cell geometry and uniform pore distribution. In this stage, reaction is effected until a stiff, pourable, or easily extrudable froth, which is sufficiently stable as to substantially retain the size and distribution of gas bubbles, is formed as a result of the agitation. After forming the froth, the reactants are cured in a mold at elevated temperature in the second stage.

In the first stage, the reactants are combined at an elevated temperature and subjected to agitation during the froth formation. Generally, it is preferred to add the surfactant and acid to an aqueous dispersion of the polyvinyl alcohol prior to adding the formaldehyde thereto. This is conveniently carried out by adding the surfactant and acid catalyst to the aqueous dispersion of polyvinyl alcohol at elevated temperature while conducting agitation such as with beaters in order to form an initial froth prior to adding the formaldehyde thereto. After a froth is initially formed, the formaldehyde, at elevated temperature, is added to the reaction system while continuing agitation in order to obtain a stable pore geometry necessary for high fluid capacity and fast wicking. It is preferred to add the formaldehyde subsequent to adding the wetting agent and/or catalyst to the polyvinyl alcohol since it has been found that sponges having a more uniform pore size can be obtained thereby. The formaldehyde is added as an aqueous solution, generally about 37% aqueous to the reaction system while both the reaction system and the formaldehyde are maintained at an elevated temperature of between about 85° and 140° F., preferably between about 120° and 130° F. Surprisingly, it has been found that when the reactants are maintained at these elevated temperatures during agitation while undergoing initial curing, sponge products having vastly improved liquid holding capacity and wicking characteristics are obtained as compared to sponge products obtained when the formaldehyde is added at lower temperatures, generally at room temperature.

During agitation, generally with beaters, the surrounding air is entrained in the reaction mixture to form the gas bubbles. Usually, entrainment of some relatively large bubbles accompanies the desired gas bubble size formation. In order to assure pore size uniformity and distribution, these large gas bubbles must be removed prior to curing the reaction. One method for removing these gas bubbles comprises reversing the direction of agitation and reverse mixing slowly so that they may rise to the surface and be removed from the reaction system. Alternatively, the froth can be extruded through a sieve or equivalent means such as a mesh screen to remove oversized gas bubbles from the froth.

After the froth is formed, it is cast into a warm mold for a sufficient period of time to cure the entire sponge composition. When the froth is placed into the mold, the mold is at a temperature between about 150° and 170° F. so that the pore geometry size and distribution induced therein by the prior agitation step is substantially maintained by initiating polymerization. The mold and its contents are then heated initially to a relatively high temperature of between about 150° and 170° F. and more preferably between about 160° and about 165° F., so that the exterior portion of the composition continues to cure relatively quickly and forms a framework which maintains the volume of the rest of the foam during subsequent curing thereof. By following this procedure, it has been found that the uniformity of pore size distribution is maintained thereby. Thereafter, the remaining portion of the foam is cured at a temperature of between about 80° and about 140° F., preferably between about 80° and about 110° F., so that the remaining portion of the uncured foam cures uniformly. If the foam was cured at the higher initial curing temperatures only to accelerate the cure time, uneven curing would be observed since the foam is a relatively poor transmitter of heat from the exterior of the mold to the interior of the foam and the outside would shrink excessively. Similarly, if curing is conducted at temperatures lower than these desired curing temperatures, the curing time would be excessive so that the gas bubbles would have time to merge increasingly into larger bubbles thereby destroying the uniformity and size of pore desired.

The formaldehyde employed herein comprises aqueous solutions of formaldehyde. It has been found that other sources of formaldehyde, e.g. paraformaldehyde or hexamethylenetetramine, residues of which are toxic, are not desirable for forming the products of this invention unless converted to formaldehyde beforehand, since they are more difficult to remove from the sponge product prior to use. In contrast, the formaldehyde remaining after reaction when employed as a pure aqueous solution is relatively easy to remove from the sponge by washing with water to obtain non-toxic levels of formaldehyde.

The preferred polyvinyl alcohols employed herein are the medium molecular weight range polyvinyl alcohols since it has been found that improved uniformity of pore size can be obtained therewith. Generally, the medium molecular weight polyvinyl alcohols have an average molecular weight of between about 35,000 and about 45,000, more usually between about 39,000 and about 42,000. The molecular weight of polyvinyl alcohols can be determined by measuring the viscosity by means well known in the art.

Any inorganic acid catalyst may be employed in the process of this invention to effect reaction of the formaldehyde and the polyvinyl alcohol. In contrast, organic acids such as toluene sulfonic acid are not useful in the process of this invention since they are more difficult to remove from the sponge product and, if present in the sponge product would present a serious toxicological problem. Representative suitable inorganic acids include sulfuric acid, hydrochloric acid, phosphoric acid, nitric acid and the mixture thereof. Generally, these acids are added as aqueous solutions to the reaction mixture and the amount of acid employed is generally between about 75 and about 200 weight percent based upon the weight of the polyvinyl alcohol.

The relative proportions of formaldehyde and polyvinyl alcohol are regulated so as to effect reaction of between about 25 and about 55%, preferably between about 30 and about 40% of the hydroxyl groups of the polyvinyl alcohol. When less than about 25% of the hydroxyl groups are reacted, the resultant sponge exhibits undesirably weak mechanical properties and, therefore, is not useful. In contrast, when more than about 55% of the hydroxyl groups are reacted, the resultant product is stronger but more abrasive to such a degree as to render it not reasonably useful as a medical sponge.

The surfactants employed herein are those which promote formation of a stable froth in small quantities and do not present a serious toxicological hazard. Representative suitable surfactants include Triton X-100, Triton X-200 and sodium lauryl sulfates or the like. These surfactants are relatively non-toxic and can be removed subsequently from the sponge by washing. The surfactant is employed in amounts of between about 2 and about 6 weight % of polyvinyl alcohol. Increased amounts of surfactant result in stiffer foams prior to curing and promote the formation of sponges having a relatively small pore size. In contrast, when employing relatively low amounts of the surfactant in the order of about 0.5 to about 2 weight % based upon the polyvinyl alcohol, the resultant sponge exhibits a relatively large non-uniform pore size. In any event, the surfactant is removed from the sponge after it is cured by washing with deionized water.

After the reaction mixture has been cured in the mold to form a sponge, the sponge is removed therefrom and washed with deionized water and squeezed to remove the elutable unreacted formaldehyde, acid and surfactant. The alternate steps of washing and squeezing are repeated until substantially all of the elutable surfactant, formaldehyde and acid are removed from the sponge. The alternate washing and drying is continued until a pH of 2–3 occurs in the washwater as measured by pH paper. Usually, this requires between about 10 to 15 sequential washings and squeezings. The final washing steps are completed after freezing and cutting the sponge into desired shapes. The preliminary washed sponge then is frozen and cut into smaller sponges of a desired shape in a manner so as to eliminate or minimize any lint formation, that might occur during the cutting operation. Cutting is preceded by freezing the damp sponge and then cutting the sponge with a cutting tool. It has been found that by freezing the liquid in the sponge, the friction on the cutting tool during cutting is minimized thereby minimizing lint formation resulting from fibers being torn from the sponge. The whole sponge or pieces from the cut sponge are dried in a manner so that upon rewetting and expansion they retain their general shape. It is essential that medical sponges maintain their general shape in both the wet and dry state since this characteristic is essential in some surgical procedures. For example, with eye spear sponges, it is necessary that the shape thereof be predictable in order to assure uniform absorption and contact with the liquid from the eye during eye surgery with no rough edges to catch on fine sutures. Alternatively, surgical sponges placed against internal organs during surgery should expand uniformly to avoid undue local pressure on the organ. Shape maintaining while drying is effected by placing the sponge sheets between vapor-porous pads such as open celled polyurethane foam sheets and subjected first to a temperature of between 150° and 160° F. so that the outer surfaces of the sponge are quickly dried and rendered relatively stiff in comparison with the interior of the sponge. This provides a relatively stable shape to the sponge being dried so that in a second step, the interior of the sponge can be subjected to moderate temperatures wherein the heat penetrates into the interior of the sponge uniformly to effect vaporization of the liquid therein out through the vapor-porous material. If such a procedure were not followed, the dried sponge would not be subjected to heat uniformly and would distort during drying due to uneven shrinkage and, upon subsequent wetting of the sponge parts thereof, would expand non-uniformly.

The sponge then is packaged either dry or premoistened under sterile conditions. When packaged premoistened, the sponge loses less than about 3.0% of its original absorptive capacity for liquids. When moist, the sponge initially has a softer feel than the dry sponge. In some surgical applications, e.g. neurosurgery, sponges are generally premoistened by the surgeon before they are put in contact with nerve tissue.

The sponges of this invention have a greatly improved capacity for holding liquids as compared to prior art sponges including prior art sponges prepared from formaldehyde and polyvinyl alcohol. The sponges of this invention absorb water to the extent of greater than 23 times the sponge weight and usually greater than 23 times the sponge weight up to about 27 times the sponge weight. Furthermore, the sponges of this invention have instantaneous absorbency time as measured by ASTM-D1117-74-5.2 procedure. In contrast, the sponges produced from polyvinyl alcohol and formaldehyde by prior art procedure have absorbency time characteristics measured by the same procedure in excess of 20 minutes. Furthermore, the sponges of this invention expand uniformly when wet to retain their same general shape during expansion. In addition, the sponges are biocompatible in that they contain little or no elutable materials and they are lint-free, resilient and non-abrasive. Furthermore, the pore size range and pore geometry of the sponges of this invention can be controlled. The sponges of this invention can be totally colored such that in use, when contacted with blood, will provide a distinct color contrast with blood. The characteristic of controlled pore size is extremely important for forming precision sponges to be used in eye surgery or in other sponge instruments. It is preferred that these sponges contain pores of a size not exceeding about 0.5 mm. Prior to this invention, sponges having this controlled small pore size distribution have not been obtained.

In an important aspect of the present invention, a radiopaque sponge product is formed which exhibits radiopaqueness homogeneously throughout its entire structure. This is an important characteristic in surgical sponges since it permits the surgeon to determine easily whether sponges have been mistakenly left in the patient after a surgical procedure. In contrast, present sponges are rendered opaque only over a portion thereof and this renders their location difficult since they are more subject to masking. By the process of this invention, a radiopaque substance is mixed with a polyvinyl alcohol to be subsequently incorporated into the sponge reaction. Mixing is conducted so that the polyvinyl alcohol encapsulates the radiopaque substance. The polyvinyl alcohol and radiopaque substance are agitated at an elevated temperature to attain a relatively uniform slurry. Thereafter, the slurry is dried and broken up to form a powder. This powder then can be added to the reaction mixture employed to form the basic sponge composition described above, prior to curing so that the radiopaque substance is physiochemically encapsulated and thus locked within the final sponge structure. By following this procedure, a sponge product produced by the process of this invention can be cut to the desired shape while releasing little or no radiopaque material. This is important since little or no radiopaque material will be deposited into the patient upon subsequent use of the sponge. Representative suitable radiopaque materials include barium sulfate, bismuth suboxide or the like. In forming the initial encapsulated radiopaque material, the radiopaque material is employed in amounts of between about 200 and about 300 weight % based upon the weight of polyvinyl alcohol with which it is mixed initially to form the dispersible powders. The encapsulated radiopaque material formed by this procedure subsequently is employed in the froth in an amount of between about 5 and about 35 weight % based upon the weight of polyvinyl alcohol in the froth. If desired to improve visual contrast, the initial polyvinyl alcohol radiopaque powder, or sponge composition also can be admixed with a non-elutable, non-toxic pigment or dye having a color that contrasts with the color of surrounding tissue or blood.

In contrast to the process of this invention, when pure barium sulfate powder is admixed with the sponge-forming compositions of this invention, an unsatisfactory sponge product is obtained. When this latter procedure is followed, the barium sulfate is easily and undesirably washed out during manufacture and use of the sponge. This occurs because the barium sulfate is not bound as strongly as the preencapsulated barium sulfate which has reactive sites that chemically bond to the polyvinyl alcohol formaldehyde reaction system. The radiopaque sponge of this invention can be rubbed, clamped, or cut to form smaller sponges without significant loss of barium sulfate, and radiopacity.

In another aspect of this invention, the sponge can be modified to produce a catamenial tampon wherein the sponge is impregnated with a nontoxic gelling agent which has the effect of improving retention of absorbed liquids even when the sponge is subjected to moderate pressure in the order of about 10 psig. The gelling agent is solubilized in a nontoxic solvent and impregnated into the sponge. The impregnated sponge then is heated to remove the solvent and leave the dry gelling agent in the sponge. Representative suitable gelling agents include carboxymethyl cellulose, polysaccharides, poly hydrox ethyl methacrylates and acrylonitrile adducts of cellulose.

The following examples illustrate the present invention and are not intended to limit the same.

EXAMPLE 1

This example illustrates the method of this invention for forming a surgical sponge having a uniformly small pore size distribution of between about 0.1 mm and about 0.5 mm. Into a rotary beater was mixed 554 grams of a medium molecular weight fully hydrolyzed polyvinyl alcohol with 4725 grams of deionized cold water which was mixed until a smooth paste was achieved. The temperature of the paste then was raised to 180° F. and mixing was effected for about 5 minutes at this temperature. The mixture was then cooled to 115°–120° F. and 17 grams of Triton X-100 wetting agent was added and the resultant mixture was agitated for ten minutes. 815 cc of 50% sulfuric acid at a temperature of 110°–120° F. was added to the mixture and mixed so that its volume was 9800 cc. Thereafter, 585 cc of 37% aqueous formaldehyde solution at 100°–110° F. was added slowly to the mixture and was agitated for 60 seconds. The temperature of the mix was about 110°–115° F. and the volume was about 12,600 cc. The beaters then were rotated in a reverse direction at 1/6 of the original speed for one minute until the observed rise of larger bubbles in the froth ceased. Reverse mixing was continued while the mix became noticeably thicker. This froth then was extruded into a plastic mold that had been previously heated to 160° F. The froth was cured in the mold for 1 hour at 140° F. and the mold then was removed from the oven and cured at 80°–110° F. for 20 hours. Thereafter, the mold was opened and the sponge obtained was washed by alternately running it through deionized water and rubber rolls until the rinse water had a pH of not lower than 3.0. The damp sponge was cooled until frozen solid and then cut to the desired shape. The sponge slices were then defrosted and final washed until 50 cc of the wash water upon vigorous shaking did not produce a foam which maintained itself longer than 10 seconds. The sponge pieces were then placed between layers of open cell foam pads and dried while held between the pads to maintain shape and flatness of the sponge. Drying was achieved by initial case hardening at 160° F. for 1–2 hours and then maintaining at 110°–120° F. in a dehumidified chamber for one day or until the sponge is completely dry.

The sponge obtained by this procedure has uniformly distributed pore sizes within the range of between about 0.1 mm and about 0.5 mm as determined by a scale built into a stereoscopic microscope eyepiece.

The sponge had a liquid holding capacity of 21–24 times its weight as determined by ASTM D-1117-74 5.1.2 and absorbency rate of less than 10 seconds as determined by ASTM D-1117-74 5.2.

EXAMPLE 2

This example illustrates the method of this invention for forming a surgical sponge having a uniformly medium pore size of between about 0.3 mm and about 1.0 mm. Into a rotary beater was mixed 475 grams of a medium molecular weight fully hydrolyzed polyvinyl alcohol with 4050 grams of deionized cold water which was mixed until a smooth paste was achieved. The temperature of the paste then was raised to 180° F. and mixing was effected for about 5 minutes at this temperature. The mixture was then cooled to 110°–120° F. and 15 grams of Triton X-100 wetting agent was added and the resultant mixture was agitated for 5 minutes. 700 cc of 50% sulfuric acid at a temperature of 110° F. was added to the mixture and mixed so that its volume was 9800 cc. Thereafter, 500 cc of 37% aqueous formaldehyde solution at 100°–110° F. was added slowly to the mixture and was agitated for 60 seconds. The temperature of the mix was about 105° to 108° F. and the volume was about 12,600 cc. The beaters then were rotated in a reverse direction for 1 minute at 1/6 the original speed until the observed rise of larger bubbles in the froth ceased. Reverse mixing was continued while the mix became noticeably thicker. This froth then was extruded into a plastic mold that had been previously heated to 160° F. The froth was cured in the mold for 1 hour at 140° F. and the mold then was removed from the oven and cured at room temperature for 20 hours. Thereafter, the mold was opened and the sponge obtained was washed by alternately running it through deionized water and rubber rolls until the rinse water had a pH of 3 minimum. The damp sponge was cooled until frozen solid and then cut to the desired shape. The sponge slices were then defrosted and final washed until 50 cc of the wash water upon vigorous shaking did not produce a foam which maintained itself longer than 10 seconds. The sponge pieces were then placed between layers of open cell foam pads, and dried while held between the pads to maintain shape and flatness of the sponge. Drying was achieved by initial case hardening at 160° F. for 1–2 hours and then holding at 110°–120° F. in a dehumidified chamber for one day or until the sponge is completely dry.

The sponge maintained by this procedure had uniformly sized medium pores within the range of between about 0.3 mm and about 1.0 mm as determined by a scale built into the eyepiece of a stereoscopic microscope.

The sponge had a liquid holding capacity of 22–25 times its weight as determined by ASTM D-1117-74 5.1.2 and an absorbency rate of less than 10 seconds as determined by ASTM D-1117-74 5.2.

EXAMPLE 3

This example illustrates the method of this invention for forming a surgical sponge having a uniformly large pore size of about 0.5 mm and about 4.0 mm. Into a rotary beater was mixed 360 grams of a medium molecular weight fully hydrolyzed polyvinyl alcohol with 3010 grams of deionized cold water which was mixed until a smooth paste was achieved. The temperature of the paste then was raised to 180° F. and mixing was effected for about 5 minutes at this temperature. The mixture was then cooled to 110° to 120° F. and 10 grams of Triton X-100 wetting agent was added and the resultant mixture was agitated for 12 minutes at high speed. Thereafter, 525 cc of the deionized water at 120° F. was added in the mixture and then was agitated for 10 minutes. 525 cc of 50% sulfuric acid at a temperature of 110° F. was added to the mixture and mixed so that its volume was 12,000 cc. Thereafter, 375 cc of 37% aqueous formaldehyde solution at 100°–110° F. was added slowly to the mixture and was agitated for 60 seconds. The temperature of the mix was about 108° to 110° F. and the volume was about 15,000 cc. The beaters then were rotated in a reverse direction for one minute at 1/6 the original speed until the observed rise of larger bubbles in the froth ceased. Reverse mixing was continued while the mix became noticeably thicker. This froth then was extruded into a plastic mold that had been previously heated to 160° F. The froth was cured in the mold for 1 hour at 140° F. and the mold then was removed from the oven and cured at room temperature for 20 hours. Thereafter, the mold was opened and the sponge obtained was washed by alternately running it through deionized water and rubber rolls until the rinse water had a pH of 3 minimum. The damp sponge was cooled until frozen solid and then cut to the desired shape. The sponge slices were then defrosted and final washed until 50 cc of the wash water upon vigorous shaking did not produce a foam which maintained itself longer than 10 seconds. The sponge pieces were then placed between layers of open cell foam pads and dried while held between the pads to maintain shape and flatness of the sponge. Drying was achieved by initial case hardening at 160° F. for 1–2 hours and then holding at 110°–120° F. in a dehumidified chamber for one day or until the sponge is completely dry.

The sponge obtained by this procedure had uniformly sized large pores within the range of between about 0.5 mm and about 0.4 mm as determined by a scale built into the eyepiece of a stereoscopic microscope.

The sponge had a liquid holding capacity of 23–26 times its own weight as determined by ASTM D-1117-74 5.1.2 and absorbency rate of less than 10 seconds as determined by ASTM D-1117-74 5.2.

EXAMPLE 4

The sponge of Example 3 was impregnated with a 5% concentration of polyhydroxyethyl methacrylate in methyl alcohol. The alcohol was allowed to evaporate at 120° F. leaving the gel forming particles distributed homogeneously throughout the sponge matrix. The sponge was then immersed in body temperature water and allowed to completely saturate. A control sponge of exactly the same dimensions (¾ inches wide × 3 inches long) without the gel particles was saturated simultaneously with the same water. Both sponges were then subjected to a hydrostatic pressure of 7 psi, for 15 minutes and examined for appearance and water loss. The sponge containing the gel particles when swelled in water took on the appearance of a stick of jello. The control sponge was more limp to the touch and easily released water under slight pressure. The gel-containing sponge picked up 19 times its own weight while the control, 24 times its own weight in water. After application of 7 psi pressure, the sponge containing the gel retained 93% of its water while the control retained 61% of its water. The gel slowed the rate for total water saturation from 30 seconds, for the control, to about 168 seconds for the gel sponge.

EXAMPLE 5

This example illustrates the method for making a radiopaque surgical sponge by the process of this invention.

A slurry comprising 336 grams barium sulfate was mixed with 800 cc of water and mixed for about 10 minutes until all of the barium sulfate was thoroughly dispersed. 143 Grams of medium molecular weight, fully hydrolyzed polyvinyl alcohol was then added to the barium sulfate dispersion while mixing was maintained and the resultant mixture was heated until it reached 180° F. A 2% by weight of a drug and cosmetic grade approved dye, e.g. DC #6 Blue was dispersed in a 6% aqueous solution of the polyvinyl alcohol with high speed mixing in a Waring blender. 25 Grams of the dye mix was added to the slurry and mixed thoroughly therein to form a uniform blue color. The slurry was then hot poured onto a Teflon-coated tray to about ⅛-inch thickness. The trays then were placed into an oven at 200° F. and water was removed by drying until the composition was brittle to the touch. The composition then was ground through a 1 mm mesh screen.

The resultant product then was useful for being mixed with the acid catalyzed formaldehyde-polyvinyl alcohol reaction to form the sponge as described in Example 1. The encapsulated barium sulfate can be employed at about 5–25 weight % based upon the weight of the polyvinyl alcohol used to form the basic sponge.

EXAMPLE 6

This example illustrates the necessity of mixing the formaldehyde and polyvinyl alcohol reactants at elevated temperatures in order to produce a sponge having a high liquid holding capacity and fast absorption rate as required by this invention.

A sponge was made wherein the formaldehyde was at room temperature (70° F.) when added to the polyvinyl alcohol. 117 Grams of a 14½% aqueous solution of medium molecular weight polyvinyl alcohol were mixed with 70 cc water and 1.1 grams of a Triton X-100 surfactant, 70 cc of a 55% solution of sulfuric acid to which was added 25 cc of a 37% aqueous solution of formaldehyde. The polyvinyl alcohol mixture prior to formaldehyde addition was at 70°–75° F. and the added formaldehyde solution was at 70° F. The resultant solution was beaten to a froth of 1000 cc and permitted to stand for 20 hours at room temperature until cured.

The wicking rate, and liquid holding capacity of this sponge and the sponge prepared by Example 1 then were compared. Wicking rate, in each instance was determined by placing strips 4 × 1 × ¼ inch sponge into water and measuring the time required for the water to rise an inch in the sponge. In addition, capillary rise was determined by measuring the rise of water in the sponge to its maximum point without time restriction.

With the sponge prepared by Example 1, an absorption time of 9 seconds was required for 1 inch of wicking while the maximum capillary rise was 1½ inches with no change after 3 minutes. In contrast, with the sponge prepared by this example, the maximum capillary rise was ½ inch with no change after 3 minutes and absorption time to achieve up to at least 1 inch of wicking was beyond 3 minutes.

The rate of water absorptability of the two sponges also was measured by placing a drop of water on the surface of the dry sponge and determining the time required for the sponge to absorb water. With the sponge prepared by Example 1, the average time required with 6 samples was only 5 seconds. In contrast, no absorption of the water droplet was observed with the sponge prepared by this example even after 3 minutes had elapsed.

The sponge prepared by this example was visually determined to have a non-uniform pore size distribution in that approximately 10% of the pores had a diameter of about 0.25 mm and approximately 90% of the pores had a size of about 1.25 to 1.75 mm. There were very few pores having a diameter intermediate to these observed pore sizes. In contrast, the sponge produced by Example 1 had a uniform pore size distribution in that approximately equal number of pores were observed within a size range up to about 0.5 mm diameter. This latter internal pore structure is better for maximizing liquid absorptive capacity and absorption rate.

In another aspect of this invention, the sponge can be modified to produce a catamenial tampon wherein the sponge is caused to biodegrade more quickly. Accelerated biodegradeability is desirable since most catamenial tampons are carried into the municipal sewerage systems where quick decomposition of solid waste is important. The biodegradeable element is incorporated into the sponge by substituting the element for part of the polyvinyl alcohol. The sponge is made in the normal way as illustrated in Examples 1–3 hereof. Representative biodegrading elements are water swellable polysaccharides which partially react with aldehydes to form less soluble acetals. Examples are cornstarches, dextrins, partially epoxidized starches, inulins, among others. The polysaccharides were substituted for up to 30% of the polyvinyl alcohol with the effect of increased biodegradeability in direct proportion to the amount of polysaccharides substituted.

EXAMPLE 7

This example illustrates the method of this invention for forming a biodegradeable catamenial tampon. In a rotary beater, 50 grams of cornstarch sieved through a 325 mesh screen was mixed with 425 grams of a medium molecular weight fully hydrolyzed polyvinyl alcohol and further admixed with 4050 grams of deionized cold water and the entire mixture was stirred until a smooth paste was achieved. The temperature of the paste was raised to 180° F. and mixing was effected for about 5 minutes at this temperature. The mixture was then quickly cooled to 110°–120° F. and 15 grams of Triton X-100 wetting agent was added and the resultant mixture was agitated for 5 minutes. Thereafter, 700 cc of 50% sulfuric acid at a temperature of 75° F. was added to the mixture and mixed so that its volume was 9,800 cc. Thereafter, 500 cc of 37% formaldehyde solution was added slowly to the mixture and was agitated for 60 seconds. The temperature of the mixture was about 100°–105° F. and the volume was about 12,600 cc. The froth was mixed until it became noticeably thicker. This froth was then extruded into 1 inch inside diameter tubes. The froth was cured in the tubes for 1 hours at 140° F. and the tubes are removed from the oven and cured at room temperature for 20 hours. Thereafter, the mold was opened and the sponge obtained was pushed out of the tube and washed by alternately running it through deionized water and rubber rolls until the rinse water showed a neutral pH. The biodegradeability and/or fragmentation of this sponge in a given microorganism froth was about twice as fast as a sponge not containing polysaccharides.

What is claimed is:

1. A biocompatible, polymeric, elastomeric, lint-free, uniformly swellable hydrophilic sponge for medical purposes having a uniform pore geometry and pore size distribution throughout its volume comprising the inorganic acid-catalyzed reaction product of formaldehyde and polyvinyl alcohol, said sponge being characterized by an initial water absorbtion and a wicking point of a maximum of 10 seconds of contact with the body fluid and by a variation in the size of the diameter of the pores of less than about 8 to 1 as determined by a stereoscopic microscope eyepiece.

2. The sponge of claim 1 which contains a water-swellable non-toxic polymeric gelling agent.

3. The sponge of claim 1 which contains a biodegradable accelerating agent.

4. The sponge of claim 1 wherein said sponge is characterized by an absorption capacity for liquids in excess of twenty times the weight of the sponge.

5. A biocompatible, polymeric, elastomeric, lint-free, uniformly swellable hydrophilic sponge for medical purposes having a uniform pore geometry and pore distribution throughout its volume comprising the inorganic acid-catalyzed reaction product of formaldehyde and polyvinyl alcohol, said sponge being characterized by an initial water absorption and wicking point of a maximum of 10 seconds of contact with the body fluid, and by a variation in the size of the diameter of the pores of less than about 8 to 1 as determined by a stereoscopic microscope eyepiece and said sponge containing a homogeneously distributed particulate radiopaque material having a coating of polyvinyl alcohol or a reaction product of polyvinyl alcohol and formaldehyde which coating is copolymerized with said acid-catalyzed reaction product of formaldehyde and the polyvinyl alcohol.

6. The process for forming the sponge of claim 1 which comprises frothing a mixture of medium molecular weight polyvinyl alcohol, an inorganic acid and a non-toxic wetting agent at a temperature of about 85°–140° F to form an elevated temperature froth having a volume between 150 and 400% of the unfrothed mixture;

adding to said elevated temperature froth, an aqueous solution of formaldehyde at about 85°–140° F, the amount of formaldehyde being that sufficient to react with between about 25 and 55% of the hydroxyl groups of the polyvinyl alcohol, and frothing the resulting mixture at said elevated temperature until the mix becomes noticeably thicker to form a pourable and extrudeable froth having a mechanical stability sufficiently strong to substantially maintain the volume of the froth;

maintaining the resulting froth at about 140°–170° F until the exterior portion thereof cures and then maintaining the exterior cured froth at about 80°–140° F to complete the curing, whereby a sponge is formed;

eluting substantially all of the elutable acid, wetting agent and formaldehyde from said sponge; and heating the eluted sponge to dryness while maintaining its shape.

7. The process of claim 6 wherein oversized bubbles are removed from the froth prior to curing.

8. The process of claim 6 wherein prior to heating to dryness, the eluted sponge is frozen, cut into smaller sponges, and the smaller sponges are rewashed.

9. The process of claim 8 wherein the temperature during both of said frothing steps is between about 120° and 130° F.

* * * * *